US011611107B2

(12) United States Patent
Hasegawa

(10) Patent No.: US 11,611,107 B2
(45) Date of Patent: Mar. 21, 2023

(54) LITHIUM ION SECONDARY BATTERY

(71) Applicant: NEC CORPORATION, Tokyo (JP)

(72) Inventor: Takuya Hasegawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 237 days.

(21) Appl. No.: 16/646,612

(22) PCT Filed: Sep. 12, 2018

(86) PCT No.: PCT/JP2018/033820
§ 371 (c)(1),
(2) Date: Mar. 12, 2020

(87) PCT Pub. No.: WO2019/054411
PCT Pub. Date: Mar. 21, 2019

(65) Prior Publication Data
US 2020/0266491 A1 Aug. 20, 2020

(30) Foreign Application Priority Data
Sep. 13, 2017 (JP) .............................. JP2017-175586

(51) Int. Cl.
H01M 10/0569 (2010.01)
H01M 4/38 (2006.01)
(Continued)

(52) U.S. Cl.
CPC ...... *H01M 10/0569* (2013.01); *C07D 327/00* (2013.01); *H01M 4/386* (2013.01); *H01M 4/505* (2013.01); *H01M 4/525* (2013.01); *H01M 10/0525* (2013.01); *H01M 10/0568* (2013.01); *H01M 2220/20* (2013.01);
(Continued)

(58) Field of Classification Search
CPC ........... H01M 4/38–386; H01M 4/505; H01M 4/525; H01M 10/0569; H01M 10/0525; H01M 10/0568
See application file for complete search history.

(56) References Cited

U.S. PATENT DOCUMENTS 10,446,847 B2 * 10/2019 Okada .................... H01G 11/32
2015/0303521 A1 * 10/2015 Sasaki ................... H01M 4/505
429/326
2017/0207459 A1 7/2017 Okada et al.

FOREIGN PATENT DOCUMENTS

| CN | 104798245 A | 7/2015 |
| CN | 106356562 A | 1/2017 |
| CN | 106663549 A | 5/2017 |
| CN | 107104245 A | 8/2017 |
| JP | 2014-013704 A | 1/2014 |

(Continued)

OTHER PUBLICATIONS

International Search Report for PCT/JP2018/033820 dated Oct. 16, 2018 [PCT/ISA/210].
(Continued)

*Primary Examiner* — Karie O'Neill Apicella
(74) *Attorney, Agent, or Firm* — Sughrue Mion, PLLC

(57) ABSTRACT

A purpose of the present invention is to provide a lithium ion secondary battery which has further improved life characteristics. The lithium ion secondary battery of the present invention is characterized by comprising a positive electrode comprising a positive electrode active material that operates at 4.5 V or more with respect to lithium, and an electrolyte solution comprising an electrolyte solvent comprising a fluorinated ether, a cyclic sulfonic acid ester and LiN$(FSO_2)_2$.

10 Claims, 1 Drawing Sheet

(51) Int. Cl.
*H01M 4/505* (2010.01)
*H01M 4/525* (2010.01)
*H01M 10/0525* (2010.01)
*H01M 10/0568* (2010.01)
*C07D 327/00* (2006.01)

(52) U.S. Cl.
CPC .............. *H01M 2300/004* (2013.01); *H01M 2300/0034* (2013.01); *H01M 2300/0091* (2013.01)

(56) References Cited

FOREIGN PATENT DOCUMENTS

| | | |
|---|---|---|
| JP | 2015-179661 A | 10/2015 |
| JP | 2017-084739 A | 5/2017 |
| JP | 2017-091993 A | 5/2017 |
| JP | 2017-147184 A | 8/2017 |
| WO | 2013/183655 A1 | 12/2013 |
| WO | 2014/080870 A1 | 5/2014 |
| WO | 2016/016383 A1 | 2/2016 |
| WO | 2016/152991 A1 | 9/2016 |

OTHER PUBLICATIONS

Japanese Office Action for JP Application No. 2019-542264 dated Mar. 2, 2021 with English Translation.
CN Office Action for CN Application No. 201880058871.5, dated Nov. 18, 2022 with English Translation.

\* cited by examiner

LITHIUM ION SECONDARY BATTERY

CROSS REFERENCE TO RELATED APPLICATIONS

This application is a National Stage of International Application No. PCT/JP2018/033820 filed Sep. 12, 2018, claiming priority based on Japanese Patent Application No. 2017-175586 filed Sep. 13, 2017.

TECHNICAL FIELD

The present invention relates to a lithium ion secondary battery, a manufacturing method thereof and a vehicle equipped with a lithium ion secondary battery.

BACKGROUND ART

Lithium ion secondary batteries are used in various applications. Accordingly, there is a demand for a lithium ion secondary battery that has high energy density and excellent life characteristics, but batteries having high energy density have a problem in that battery performance may deteriorate due to decomposition of an electrolyte solvent. For this reason, there is also a demand for a high durable electrolyte solvent.

It is known that $LiN(FSO_2)_2$ reacts with a positive electrode and/or a negative electrode to form on an electrode surface a coating film having an effect of preventing decomposition of an electrolyte solution. For this reason, the use of $LiN(FSO_2)_2$ in an electrolyte solution has been studied to improve battery life characteristics. Patent Documents 1 and 2 disclose battery life characteristics can be improved by adding 0.5 weight % of $LiN(FSO_2)_2$ into an electrolyte solution.

CITATION LIST

Patent Literature

Patent Document 1: WO2013/183655
Patent Document 2: WO2014/080870

SUMMARY OF INVENTION

Technical Problem

Since constituting members of an lithium ion secondary battery corrode in a non-aqueous electrolyte solution containing an imide lithium salt, such as $LiN(FSO_2)_2$, as a main electrolyte when the battery is operated at high voltage, there is a problem in that when the addition amount of $LiN(FSO_2)_2$ in an electrolyte solution is further increased, on the contrary battery life characteristics are degraded. For this reason, the addition amount of $LiN(FSO_2)_2$ is limited to small amounts such as 0.5 weight % in Patent Documents 1 and 2, and the effect of improving life characteristics is small. In view of the above mentioned problem, a purpose of the present invention is to provide a lithium ion secondary battery which has further improved life characteristics.

Solution to Problem

The first lithium ion secondary battery according to the present invention comprises:
a positive electrode comprising a positive electrode active material that operates at 4.5 V or more with respect to lithium and
an electrolyte solution comprising an electrolyte solvent comprising
a fluorinated ether represented by formula (1),
a cyclic sulfonic acid ester represented by formula (2) and $LiN(FSO_2)_2$.

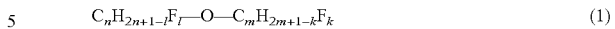

wherein n is 1, 2, 3, 4, 5 or 6, m is 1, 2, 3 or 4, l is an integer of 0 to 2n+1, k is an integer of 0 to 2m+1, and at least one of l and k is 1 or more.

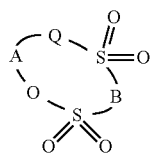

(2)

wherein Q represents an oxygen atom, a methylene group or a single bond, A represents a substituted or unsubstituted alkylene group having 1 to 6 carbon atoms, a carbonyl group, a sulfinyl group, a substituted or unsubstituted fluoroalkylene group having 1 to 6 carbon atoms or a group having 2 to 6 carbon atoms in which alkylene units or fluoroalkylene units are bonded through an ether bond, and B represents a substituted or unsubstituted alkylene group having 1 to 6 carbon atoms, a substituted or unsubstituted fluoroalkylene group having 1 to 6 carbon atoms or an oxygen atom.

Advantageous Effects of Invention

According to the present invention, it is possible to provide a lithium ion secondary battery which has improved life characteristics.

DESCRIPTION OF EMBODIMENTS

Figure 1:
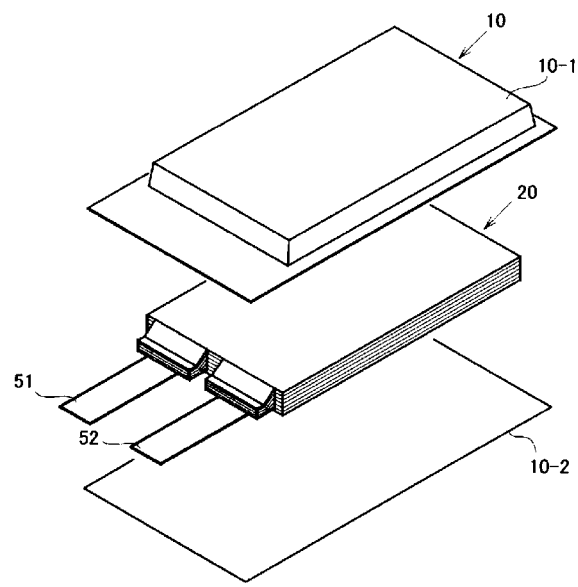
FIG. 1 is an exploded perspective view showing a basic structure of a film package battery.

Hereinafter, one example of the lithium ion secondary battery of the present embodiment will be described for each component.

<Electrolyte Solution>

The electrolyte solution of the lithium ion secondary battery of the present embodiment comprises an electrolyte solvent comprising a fluorinated ether, $LiN(FSO_2)_2$ and a cyclic sulfonic acid ester.

In the present embodiment, the electrolyte solution comprises a fluorinated ether represented by the following formula (3) as an electrolyte solvent. The fluorinated ether has an effect of assisting in the formation of the coating film derived from the cyclic sulfonic acid ester. Battery life characteristics can be improved by using the fluorinated ether as an electrolyte solvent.

wherein n is 1, 2, 3, 4, 5 or 6, m is 1, 2, 3 or 4, l is an integer of 0 to 2n+1, k is an integer of 0 to 2m+1, and at least one of l and k is 1 or more.

The fluorine substitution ratio of an alkyl group in the fluorinated ether is preferably 20% or more and 100% or less. The fluorinated ether having a high fluorine substitution ratio is suitable for a high potential positive electrode because the oxidation resistance of the electrolyte solution is improved by increasing the fluorine substitution amount. If the fluorine substitution amount is too high, the solubility of a supporting salt or the like decreases, and the battery capacity decreases in some cases. The fluorine substitution ratio is more preferably 30% or more and 95% or less, and still more preferably 40% or more and 90% or less. In formula (3), it is preferable that both of two alkyl groups are fluorine-containing alkyl groups because the oxidation resistance is high. In this specification, the term, "fluorine substitution ratio" represents the ratio of the number of fluorine atoms to the total number of hydrogen atoms and fluorine atoms in a fluorine-containing compound (fluorinated compound) or a functional group contained in the fluorine-containing compound.

Examples of the fluorinated ether represented by formula (3) include 2,2,3,3,3-pentafluoropropyl 1,1,2,2-tetrafluoroethyl ether, 1,1,2,2-tetrafluoroethyl 2,2,2-trifluoroethyl ether, 1H,1H,2'H,3H-decafluorodipropyl ether, 1,1,2,3,3,3-hexafluoropropyl 2,2-difluoroethyl ether, isopropyl 1,1,2,2-tetrafluoroethyl ether, propyl 1,1,2,2-tetrafluoroethyl ether, 1,1,2,2-tetrafluoroethyl 2,2,3,3-tetrafluoropropyl ether (FE), 1H,1H,5H-perfluoropentyl 1,1,2,2-tetrafluoroethyl ether, 1H-perfluorobutyl 1H-perfluoroethyl ether, methyl perfluoropentyl ether, methyl perfluorohexyl ether, methyl 1,1,3,3,3-pentafluoro-2-(trifluoromethyl)propyl ether, 1,1,2,3,3,3-hexafluoropropyl 2,2,2-trifluoroethyl ether, ethyl nonafluorobutyl ether, ethyl 1,1,2,3,3,3-hexafluoropropyl ether, 1H,1H,5H-octafluoropentyl 1,1,2,2-tetrafluoroethyl ether, 1H,1H,2'H-perfluorodipropyl ether, heptafluoropropyl 1,2,2,2-tetrafluoroethyl ether, 1,1,2,2-tetrafluoroethyl-2,2,3,3-tetrafluoropropyl ether, 2,2,3,3,3-pentafluoropropyl 1,1,2,2-tetrafluoroethyl ether, ethyl nonafluorobutyl ether, methyl nonafluorobutyl ether, 1,1-difluoroethyl 2,2,3,3-tetrafluoropropyl ether, bis(2,2,3,3-tetrafluoropropyl)ether, 1,1-difluoroethyl 2,2,3,3,3-pentafluoropropyl ether, 1,1-difluoroethyl 1H, 1H-heptafluorobutyl ether, 2,2,3,4,4,4-hexafluorobutyl difluoromethyl ether, bis(2,2,3,3,3-pentafluoropropyl)ether, nonafluorobutyl methyl ether, bis(1H,1H-heptafluorobutyl) ether, 1,1,2,3,3,3-hexafluoropropyl 1H,1H-heptafluorobutyl ether, 1H,1H-heptafluorobutyl trifluoromethyl ether. 2,2-difluoroethyl 1,1,2,2-tetrafluoroethyl ether, bis(trifluoroethyl)ether, bis(2,2-difluoroethyl)ether, bis(1,1,2-trifluoroethyl)ether, 1,1,2-trifluoroethyl 2,2,2-trifluoroethyl ether, bis(2,2,3,3-tetrafluoropropyl)ether and the like.

Among these, from the viewpoint of voltage resistance properties and boiling point, it is preferable to use at least one fluorinated ether selected from 1,1,2,2-tetrafluoroethyl 2,2,3,3-tetrafluoropropyl ether, 2,2,3,4,4,4-hexafluorobutyl difluoromethyl ether, 1,1-difluoroethyl 2,2,3,3-tetrafluoropropyl ether, 1,1,2,3,3,3-hexafluoropropyl 2,2-difluoroethyl ether, 1,1-difluoroethyl 1H,1H-heptafluorobutyl ether, 1H,1H,2'H,3H-decafluorodipropyl ether, bis(2,2,3,3,3-pentafluoropropyl)ether, 1H,1H,5H-perfluoropentyl 1,1,2,2-tetrafluoroethyl ether, bis(1H,1H-heptafluorobutyl)ether, 1H,1H,2'H-perfluorodipropyl ether, 1,1,2,3,3,3-hexafluoropropyl 1H,1H-heptafluorobutyl ether, 1H-perfluorobutyl 1H-perfluoroethyl ether, bis(2,2,3,3-tetrafluoropropyl)ether.

The fluorinated ether may be used singly or in combination of two or more. When two or more kinds of the fluorinated ethers are used in combination, cycle characteristics of the lithium ion secondary battery may be improved, compared to the case where only one kind of the fluorinated ether is used.

The content of the fluorinated ether in the electrolyte solvent is preferably 1 volume % or more, more preferably 5 volume % or more, and still more preferably 10 volume % or more. Containing too small of the fluorinated ether may increase the viscosity of the electrolyte solution to thereby decrease the electrical conductivity and elicit a drop in the capacity. The content of the fluorinated ether in the electrolyte solvent is preferably 90 volume % or less, more preferably 70 volume % or less, and still more preferably 50 volume % or less. Containing too much of fluorinated ether induces a decrease in the dielectric constant of the electrolyte solution, thereby a supporting salt becomes impossible to dissociate, and a drop in the capacity may be occurred as well.

In the present embodiment, the electrolyte solution may further comprise a carbonate ester compound as an electrolyte solvent. Examples of the carbonate ester compound include, but not particularly limited to, those represented by the following formula (4).

$$R_1-O-\underset{\underset{O}{\|}}{C}-O-R_2 \qquad (4)$$

wherein $R_1$ and $R_2$ each independently represent an alkyl group. A carbon atom of $R_1$ and a carbon atom of $R_2$ may be bonded via a single bond or a double bond to form a cyclic structure.

In formula (4), $R_1$ and $R_2$ may have a substituent. The substituent may include halogen atoms (for example, chlorine atom, bromine atom, fluorine atom) and the like, and the substituent is preferably a fluorine atom.

In formula (4), alkyl groups of $R_1$ and $R_2$ each independently preferably have 1 to 10 carbon atoms, and more preferably have 1 to 5 carbon atoms.

The carbonate ester compounds include cyclic carbonates and open-chain carbonates. Examples of the carbonate ester compound include ethylene carbonate (EC), propylene carbonate (PC), butylene carbonate (BC), vinylene carbonate (VC), dimethyl carbonate (DMC), diethyl carbonate (DEC), ethylmethyl carbonate (MEC), dipropyl carbonate (DPC) and the like, and a part or all of hydrogen atoms in their alkyl groups or alkylene groups may be replaced by a halogen atom, preferably a fluorine atom. For example, 4-fluoro-1,3-dioxolan-2-one (monofluoroethylene carbonate (FEC)), (cis or trans)4,5-difluoro-1,3-dioxolan-2-one, 4,4-difluoro-1,3-dioxolan-2-one, 4-fluoro-5-methyl-1,3-dioxolan-2-one or the like may be used as the fluorinated cyclic carbonate.

The content of the carbonate ester compound in the electrolyte solvent is preferably 5 volume % or more, more preferably 10 volume % or more, and still more preferably 40 volume % or more. The content of the carbonate ester compound in the electrolyte solvent is preferably 97 volume % or less, more preferably 90 volume % or less, and still more preferably 80 volume % or less. Containing too small of the carbonate ester compound may decrease the electrical conductivity of the electrolyte solution to thereby degrade cycling characteristics. Containing too much of the carbonate ester compound may increase gas generation because the carbonate ester compound easily decompose at a high potential.

In the present embodiment, the electrolyte solution may further comprise a fluorinated phosphate ester as an electrolyte solvent. Examples of the fluorinated phosphate ester include, but not particularly limited to, those represented by the following formula (5).

$$O=P(-O-R_1')(-O-R_2')(-O-R_3') \quad (5)$$

wherein $R_1'$, $R_2'$ and $R_3'$ are each independently an alkyl group or a fluorine-containing alkyl group, and at least one of $R_1'$, $R_2'$ and $R_3'$ comprises fluorine.

In formula (5), alkyl groups of $R_1'$, $R_2'$ and $R_3'$ each independently have 1 to 5 carbon atoms, and more preferably have 1 to 3 carbon atoms.

Examples of the fluorinated phosphate ester include 2,2,2-trifluoroethyl dimethyl phosphate, bis(trifluoroethyl) methyl phosphate, bistrifluoroethyl ethyl phosphate, tris(trifluoromethyl) phosphate, pentafluoropropyl dimethyl phosphate, heptafluorobutyl dimethyl phosphate, trifluoroethyl methyl ethyl phosphate, pentafluoropropyl methyl ethyl phosphate, heptafluorobutyl methyl ethyl phosphate, trifluoroethyl methyl propyl phosphate, pentafluoropropyl methyl propyl phosphate, heptafluorobutyl methyl propyl phosphate, trifluoroethyl methyl butyl phosphate, pentafluoropropyl methyl butyl phosphate, heptafluorobutyl methyl butyl phosphate, trifluoroethyl diethyl phosphate, pentafluoropropyl diethyl phosphate, heptafluorobutyl diethyl phosphate, trifluoroethyl ethyl propyl phosphate, pentafluoropropyl ethyl propyl phosphate, heptafluorobutyl ethyl propyl phosphate, trifluoroethyl ethyl butyl phosphate, pentafluoropropyl ethyl butyl phosphate, heptafluorobutyl ethyl butyl phosphate, trifluoroethyl dipropyl phosphate, pentafluoropropyl dipropyl phosphate, heptafluorobutyl dipropyl phosphate, trifluoroethyl propyl butyl phosphate, pentafluoropropyl propyl butyl phosphate, heptafluorobutyl propyl butyl phosphate, trifluoroethyl dibutyl phosphate, pentafluoropropyl dibutyl phosphate, heptafluorobutyl dibutyl phosphate, tris(2,2,3,3-tetrafluoropropyl) phosphate, tris(2,2,3,3,3-pentafluoropropyl) phosphate, tris(2,2,2-trifluoroethyl) phosphate, tris(1H,1H-heptafluorobutyl) phosphate, tris(1H,1H,5H-octafluoropentyl) phosphate and the like.

The fluorinated phosphate ester may be used singly or in combination of two or more. When two or more kinds of the fluorinated phosphate esters are used in combination, the lithium ion secondary battery having excellent cycle characteristics may be provided.

The fluorinated phosphate ester has advantages that its oxidation resistance is high and it is hardly decomposed. In addition, it is thought that it has also the effect of suppressing gas generation. On the other hand, since the viscosity is high and the dielectric constant is comparatively low, when the content is excessively large, the conductivity of the electrolyte solution decreases. The content of the fluorinated phosphate ester in the electrolyte solvent is preferably 1 to 80 volume %, more preferably 5 to 70 volume % and still more preferably 10 to 60 volume %.

In the present embodiment, the electrolyte solution may further comprise a sulfone compound as an electrolyte solvent. Examples of the sulfone compound include, but not particularly limited to, those represented by the following formula (6).

$$R_1''-SO_2-R_2'' \quad (6)$$

wherein $R_1''$ and $R_2''$ each independently represent an alkyl group. A carbon atom of $R_1''$ and a carbon atom of $R_2''$ may be bonded through a single bond or a double bond to form a cyclic structure.

In formula (6), the number of carbons n1 in $R_1''$ and the number of carbons n2 in $R_2''$ are each independently preferably $1 \leq n1 \leq 12$ and $1 \leq n2 \leq 12$, more preferably $1 \leq n1 \leq 6$ and $1 \leq n2 \leq 6$, and further preferably $1 \leq n1 \leq 3$ and $1 \leq n2 \leq 3$. The alkyl group also includes open-chain, branched-chain, and cyclic ones.

$R_1''$ and $R_2''$ may have a substituent, and examples of the substituent include alkyl groups having 1 to 6 carbon atoms (for example, methyl group, ethyl group, propyl group, isopropyl group, butyl group, and isobutyl group), aryl groups having 6 to 10 carbon atoms (for example, phenyl group and naphthyl group), halogen atoms (for example, a chlorine atom, bromine atom, and fluorine atom) and the like.

Examples of the sulfone compound include cyclic sulfone compounds including sulfolane (i.e. tetramethylene sulfone), methylsulfolanes such as 3-methylsulfolane, 3,4-dimethylsulfolane, 2,4-dimethylsulfolane, trimethylene sulfone (thietane 1,1-dioxide), 1-methyl trimethylene sulfone, pentamethylene sulfone, hexamethylene sulfone and ethylene sulfone; and open-chain sulfone compounds including dimethyl sulfone, ethyl methyl sulfone (EMS), diethyl sulfone, butyl methyl sulfone, dibutyl sulfone, methyl isopropyl sulfone, diisopropyl sulfone, methyl tert-butyl sulfone, butyl ethyl sulfone, butyl propyl sulfone, butyl isopropyl sulfone, di-tert-butyl sulfone, diisobutyl sulfone, ethyl isopropyl sulfone (EiPS), ethyl isobutyl sulfone, tert-butyl ethyl sulfone, propyl ethyl sulfone, isobutyl isopropyl sulfone, butyl isobutyl sulfone and isopropyl (1-methyl-propyl) sulfone. Among these, at least one selected from sulfolane, 3-methyl sulfolane, dimethyl sulfone, ethyl methyl sulfone, and ethyl isopropyl sulfone is preferable.

These sulfone compounds may be used singly or in combination of two or more thereof. In one aspect of the present embodiment, it is possible to use in combination of a cyclic sulfone compound and an open-chain sulfone compound.

The sulfone compounds have a characteristic that the dielectric constant is comparatively high, facilitate dissociation of a supporting salt of the electrolyte solution, and have the effect of increasing the electrical conductivity of the electrolyte solution. Also, the sulfone compounds have characteristics that the oxidation resistance is high and gas is less generated even at a high temperature operation. On the other hand, since the sulfone compounds have high viscosity, if the concentration thereof is excessively high, the ion conductivity conversely decreases. For these reasons, the content of the sulfone compound in the electrolyte solvent is preferably 1 to 80 volume %, more preferably 2 to 70 volume %, and still more preferably 5 to 60 volume %.

In the present embodiment, the electrolyte solution comprises a cyclic sulfone acid ester. The cyclic sulfone acid ester forms a protective coating film on the positive electrode. This protective coating film can prevent the corrosion caused by $LiN(FSO_2)_2$. For this reason, the electrolyte solution comprising the cyclic sulfone acid ester can improve battery life characteristics. In particular, when a battery comprises a positive electrode active material that operates at a potential of 4.5 V or more as in the present embodiment, since $LiN(FSO_2)_2$ easily corrodes constituting members of the lithium ion secondary battery, the effect of the coating film derived from the cyclic sulfone acid ester can be enhanced. For example, the cyclic sulfone acid ester may be represented by the following formula (7).

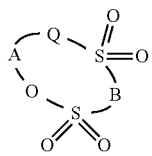
(7)

wherein Q represents an oxygen atom, a methylene group or a single bond, A represents a substituted or unsubstituted alkylene group having 1 to 6 carbon atoms, a carbonyl group, a sulfinyl group, a substituted or unsubstituted fluoroalkylene group having 1 to 6 carbon atoms or a group having 2 to 6 carbon atoms in which alkylene units or fluoroalkylene units are bonded through an ether bond, and B represents a substituted or unsubstituted alkylene group having 1 to 6 carbon atoms, a substituted or unsubstituted fluoroalkylene group having 1 to 6 carbon atoms or an oxygen atom.

In formula (7), Q represents an oxygen atom, a methylene group or a single bond, and preferably represents an oxygen atom.

In formula (7), A represents a substituted or unsubstituted alkylene group having 1 to 6 carbon atoms; a carbonyl group; a sulfinyl group; a substituted or unsubstituted fluoroalkylene group having 1 to 6 carbon atoms; or a group having 2 to 6 carbon atoms in which alkylene units or fluoroalkylene units are bonded through an ether bond. In formula (7), when A represents an alkylene group, it may be either straight or branched, and is preferably straight. In the case of a straight alkylene group, the alkylene group is represented by $—(CH_2)_n—$ (n is an integer of 1 to 6), is more preferably a methylene group or an ethylene group represented by $—(CH_2)_n—$ (n is 1 or 2), and is furthermore preferably a methylene group. In the branched alkylene group, at least one hydrogen atom of the alkylene group represented by $—(CH_2)_n—$ (n is an integer of 1 to 5) is substituted with an alkyl group, and examples of the branched alkylene group include $—C(CH_3)_2—$, $—C(CH_3)(CH_2CH_3)—$, $—C(CH_2CH_3)_2—$, $—CH(C_mH_{2m+1})—$ (m is an integer of 1 to 4), $—CH_2—C(CH_3)_2—$, $—CH_2—CH(CH_3)—$, $—CH(CH_3)—CH(CH_3)—$, $—CH(CH_3)CH_2CH_2—$, $—CH(CH_3)CH_2CH_2CH_2—$ and the like. The fluoroalkylene group means a group in which at least one of the hydrogen atoms in the foregoing alkylene group is substituted with a fluorine atom. All the hydrogen atoms may be substituted with fluorine atoms, and the position and the number of the fluorine substitution are arbitrary. The fluoroalkylene group may either be straight or branched, and is preferably straight. In the straight fluoroalkylene group in which all the hydrogen atoms are substituted with fluorine atoms, A is represented by $—(CF_2)_n—$ (n is an integer of 1 to 6). Specifically, examples of the fluoroalkylene group include monofluoromethylene group, difluoromethylene group, monofluoroethylene group, difluoroethylene group, trifluoroethylene group and tetrafluoroethylene group.

Examples of "a divalent group having 2 to 6 carbon atoms in which alkylene units or fluoroalkylene units are bonded through an ether bond" in A include $—R^4—O—R^5—$ ($R^4$ and $R^5$ each independently represent an alkylene group or a fluoroalkylene group, and the total number of carbon atoms of $R^4$ and $R^5$ is 2 to 6), and $—R^6—O—R^7—O—R^8—$ ($R^6$, $R^7$ and $R^8$ each independently represent an alkylene group or a fluoroalkylene group, and the total number of carbon atoms of $R^6$, $R^7$ and $R^8$ is 3 to 6). $R^4$ and $R^5$ may both be alkylene groups or fluoroalkylene groups, or one of them may be an alkylene group and the other may be a fluoroalkylene group. $R^6$, $R^7$ and $R^8$ may each independently be an alkylene group or a fluoroalkylene group. Examples thereof include $—CH_2—O—CH_2—$, $—CH_2—O—C_2H_4—$, $—C_2H_4—O—C_2H_4—$, $—CH_2—O—CH_2—O—CH_2—$, $—CH_2—O—CHF—$, $—CH_2—O—CF_2—$, $—CF_2—O—CF_2—$, $—C_2F_4—O—C_2F_4—$, $—CF_2—O—CF_2—O—CF_2—$ and $—CH_2—O—CF_2—O—CH_2—$.

In formula (7), B represents a substituted or unsubstituted alkylene group having 1 to 6 carbon atoms; a substituted or unsubstituted fluoroalkylene group having 1 to 6 carbon atoms; or an oxygen atom. B may either be straight or branched. Examples of the alkylene group and the fluoroalkylene group may include groups described above. Among these, B is preferably a methylene group ($—CH_2—$) or $—CH(C_mH_{2m+1})—$ (m is an integer of 1 to 4), more preferably a methylene group, an ethylidene group [$—CH(CH_3)—$] or $—CH(C_2H_5)—$, still more preferably $—CH(CH_3)—$ or a methylene group.

In formula (7), A and B may have a substituent. Examples of the substituent include alkyl groups having 1 to 6 carbon atoms (for example, methyl group, ethyl group, propyl group, isopropyl group, butyl group, and isobutyl group), aryl groups having 6 to 10 carbon atoms (for example, phenyl group and naphthyl group), halogen atoms (for example, a chlorine atom and bromine atom) and the like.

The cyclic sulfone acid ester preferably has a six-membered ring or a seven-membered ring, and examples of such a compound include methylene methanedisulfonic acid ester (MMDS), ethylene methanedisulfonic acid ester (EMDS) and 3-methyl-1,5,2,4-dioxadithiane-2,2,4,4,-tetraoxide (3MDT).

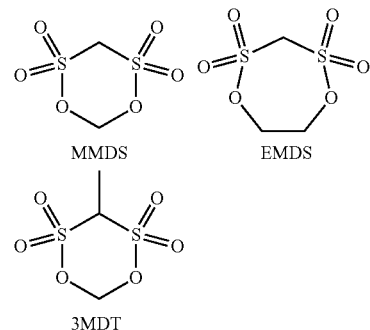

MMDS  EMDS

3MDT

The cyclic sulfone acid ester may be used singly or in combination of two or more.

The content of the cyclic sulfone acid ester in the electrolyte solution is preferably 0.3 weight % or more, more preferably 0.4 weight % or more, and still more preferably 0.7 weight % or more. The content of the cyclic sulfone acid ester in the electrolyte solution is preferably 10 weight % or less, more preferably 5 weight % or less, and still more preferably 1.5 weight % or less. When the content is excessively small, the effect of the coating film cannot be sufficiently provided, and when the content is excessively large, the internal resistance may be increased.

The electrolyte solution may further comprise a cyclic dicarboxylic acid ester. The combination of the cyclic sulfone acid ester and the cyclic dicarboxylic acid ester can further improve battery life characteristics. Examples of the cyclic dicarboxylic acid ester include compounds represented by formula (8) or (9).

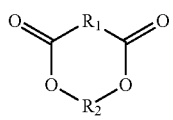

(8)

wherein $R_1$ and $R_2$ each independently represent a single bond or a substituted or unsubstituted alkylene group having 1 to 5 carbon atoms that may be branched, with the proviso that both $R_1$ and $R_2$ do not represent single bonds.

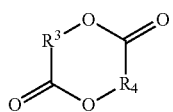

(9)

wherein $R_3$ and $R_4$ each independently represent a single bond or a substituted or unsubstituted alkylene group having 1 to 5 carbon atoms that may be branched, with the proviso that both $R_3$ and $R_4$ do not represent single bonds.

The compound represented by formula (8) or (9) is not particularly limited, but preferably have a 5 to 7-membered ring.

Examples of the compound represented by formula (8) or (9) include meldrumic acid, 1,4-dioxane-2,3-dione, 1,4-dioxane-2,5-dione, 3,6-dimethyl-1,4-dioxane-2,5-dione, 5-methyl-1,3-dioxolane-2,4-dione and the like. These may be used singly or in combination of two or more.

The content of the cyclic dicarboxylic acid ester in the electrolyte solution is preferably 0.1 weight % or more, and more preferably 0.3 weight % or more. The content of the cyclic dicarboxylic acid ester in the electrolyte solution is preferably 10 weight % or less, and more preferably 5 weight % or less.

In the present embodiment, the electrolyte solution comprises $LiN(FSO_2)_2$ as a supporting salt. $LiN(FSO_2)_2$ dissociates in the electrolyte solution to generate $N(FSO_2)_2$ anion (FSI anion), which forms, onto a positive electrode and negative electrode, an SEI coating film preventing reactions between active materials and the electrolyte solution. The effect of the FSI anion is more significantly elicited in a lithium ion secondary battery with a positive electrode active material that operates at 4.5 V or more than in a lithium ion secondary battery with a conventional 4V class positive electrode active material. This is probably because the SEI coating film is easily formed on a high potential positive electrode.

The concentration of $LiN(FSO_2)_2$ in the electrolyte solution is preferably 0.2 mol/L or more, more preferably 0.4 mol/L or more, and still more preferably 0.6 mol/L or more. The concentration of $LiN(FSO_2)_2$ in the electrolyte solution is preferably 3 mol/L or less, more preferably 2 mol/L or less, and still more preferably 1 mol/L or less. When $LiN(FSO_2)_2$ is present in the electrolyte solution in such a concentration range, life characteristics of the lithium ion secondary battery may be further improved.

In the present embodiment, it is preferable to further use a supporting salt other than $LiN(FSO_2)_2$ to improve cycle characteristics. Examples of the supporting salt other than $LiN(FSO_2)_2$ include $LiPF_6$, $LiAsF_6$, $LiAlCl_4$, $LiClO_4$, $LiBF_4$, $LiSbF_6$, $LiCF_3SO_3$, $LiC_4F_9SO_3$, $LiC(CF_3SO_2)_3$, $LiN(CF_3SO_2)_2$, $LiN(C_2F_5SO_2)_2$, $LiB_{10}Cl_{10}$ and the like. In addition, the supporting salt includes lower aliphatic lithium carboxylate, chloroboran lithium, lithium tetraphenylborate, LiBr, LiI, LiSCN, LiCl and the like. Among them, $LiPF_6$ is especially preferred from the viewpoint of oxidation resistance, reduction resistance, stability, and ease of dissolution. The concentration of the supporting salt other than $LiN(FSO_2)_2$ is preferably 0.01 mol/L or more, more preferably 0.2 mol/L or more, and still more preferably 0.4 mol/L or more. The concentration of the supporting salt other than $LiN(FSO_2)_2$ is preferably 3 mol/L or less, more preferably 2 mol/L or less, and still more preferably 1 mol/L or less. When the supporting salt other than $LiN(FSO_2)_2$ is present in the electrolyte solution in such a concentration range, life characteristics of the lithium ion secondary battery may be improved.

In the present embodiment, the total concentration of the supporting salts in the electrolyte solution is preferably 0.1 mol/L or more and 3 mol/L or less, and more preferably 0.5 mol/L or more and 1.5 mol/L or less.

<Positive Electrode>

The positive electrode comprises a current collector and a positive electrode active material layer comprising a positive electrode active material and a binder. In the present embodiment, the positive electrode active material layer comprises a positive electrode active material that operates at a potential of 4.5 V or more with respect to lithium.

For example, a lithium manganese composite oxide represented by following formula (A) can be used as the positive electrode active material that operates at a potential of 4.5 V or more.

$$Li_a(M_xMn_{2-x-y}Y_y)(O_{4-w}Z_w) \tag{A}$$

wherein, in formula (A), x, y, a, and w satisfy $0.4 \leq x \leq 1.2$, $0 \leq y$, $x+y<2$, $0 \leq a \leq 1.2$ and $0 \leq w \leq 1$, M is at least one selected from the group consisting of Co, Ni, Fe, Cr and Cu, Y is at least one selected from the group consisting of Li, B, Na, Mg, Al, Ti, Si, K and Ca, and Z is at least one selected from the group consisting of F and Cl.

Also, among these metal composite oxides, from the viewpoint of obtaining sufficient capacity and providing long operating life, it is preferable to use a spinel type compound represented by following formula (B) as the positive electrode active material that operates at a potential of 4.5 V or more.

$$LiNi_xMn_{2-x-y}A_yO_4 \tag{B}$$

wherein, in formula (B), x and y satisfy $0.4<x<0.6$ and $0 \leq y<0.3$, and A is at least one selected from the group consisting of Li, B, Na, Mg, Al, Ti and Si.

In formula (B), y preferably satisfies $0 \leq y<0.2$.

Examples of the spinel type compound include $Li_xMn_{1.5}Ni_{0.5}O_4$ ($0<x<2$).

Also, examples of the positive electrode active material operating at a potential of 4.5 V or more include Si composite oxides. Examples of such a Si composite oxide include compounds represented by the following formula (C).

$$Li_2MSiO_4 \tag{C}$$

wherein in formula (C), M is at least one selected from the group consisting of Mn, Fe and Co.

Also, the positive electrode active material that operates at a potential of 4.5 V or more may have a layered structure. Examples of the positive electrode active material comprising a layered structure include compounds represented by the following formula (D).

$$Li(M1_xM2_yMn_{1-x-y})O_2 \tag{D}$$

wherein, in formula (D), M1 is at least one selected from the group consisting of Ni, Co and Fe, M2 is at least one selected from the group consisting of Li, Mg and Al, and x and y satisfy $0.1 < x < 0.5$ and $0.05 < y < 0.3$.

Lithium metal composite oxides represented by the following formulae (E) to (G) may be used as the positive electrode active materials that operate at a potential of 4.5 V or more.

$$LiMPO_4 \tag{E}$$

wherein in formula (E), M is at least one selected from the group consisting of Co and Ni.

Examples of the olivine type positive electrode active material represented by formula (E) include $LiCoPO_4$ and $LiNiPO_4$.

$$Li(M_yMn_z)O_2 \tag{F}$$

wherein, in formula (F), y and z satisfy $0.1 \leq y \leq 0.67$, preferably $y \leq 0.5$, $0.3 \leq z \leq 0.9$, preferably $z \leq 0.7$ and $y+z=1$, and M is at least one selected from the group consisting of Li, Co and Ni.

$$Li(Li_xM_yMn_z)O_2 \tag{G}$$

wherein in formula (G), x, y, and z satisfy $0.1 \leq x < 0.3$, $0.1 \leq y \leq 0.4$, $0.33 \leq z \leq 0.7$ and $x+y+z=1$, and M is at least one selected from the group consisting of Li, Co and Ni.

In the present embodiment, the content of the positive electrode active material operating at a potential of 4.5 V or more with respect to lithium is preferably 30 weight % or more, more preferably 50 weight % or more, still more preferably 70 weight % or more, and may even be 100 weight %, based on the total amount of the positive electrode active material.

The binder is not particularly limited, and polyvinylidene fluoride, vinylidene fluoride-hexafluoropropylene copolymer, vinylidene fluoride-tetrafluoroethylene copolymer, polytetrafluoroethylene, polypropylene, polyethylene, polyimide, polyamide-imide, polyacrylic acid or the like may be used. Also, styrene butadiene rubber (SBR) or the like may be used. When an aqueous binder such as an SBR emulsion is used, a thickener such as carboxymethyl cellulose (CMC) can also be used. Two or more of the above binders may be mixed and used. The amount of the binder to be used is preferably 0.5 to 20 parts by weight based on 100 parts by weight of the positive electrode active material from the viewpoint of sufficient binding strength and high energy density that are in a trade-off relation with each other.

For the positive electrode active material layer, a conductive assisting agent may be added for the purpose of lowering the impedance. Examples of the conductive assisting agent include, flake-like and fibrous carbon fine particles and the like, for example, graphite, carbon black, acetylene black, vapor grown carbon fibers and the like.

As the positive electrode current collector, from the viewpoint of electrochemical stability, aluminum, nickel, copper, silver, and alloys thereof are preferred. As the shape thereof, foil, flat plate, mesh and the like are exemplified. In particular, a current collector using aluminum, an aluminum alloy, or iron-nickel-chromium-molybdenum based stainless steel is preferable. $LiN(FSO_2)_2$ may corrode the current collector such as aluminum, but in the present embodiment, since the cyclic sulfone acid ester forms a coating film on the positive electrode, the corrosion of the current collector can be prevented. Thus, battery life characteristics can be improved.

The positive electrode according to the present embodiment may be prepared, for example, by preparing a positive electrode slurry comprising the positive electrode active material, the binder and a solvent and applying this on the positive electrode current collector to form a positive electrode active material layer. Examples of a method of forming the positive electrode active material layer include a doctor blade method, a die coater method, a CVD method, a sputtering method, and the like. After forming the positive electrode active material layer in advance, a thin film of aluminum, nickel or an alloy thereof as a positive electrode current collector may be formed thereon by a method such as vapor deposition or sputtering.

<Negative Electrode>

The negative electrode comprises a current collector and a negative electrode active material layer comprising a negative electrode active material and a binder.

The negative electrode active material is not particularly limited, and examples thereof include carbon materials capable of absorbing and desorbing lithium ions (a), metals capable of being alloyed with lithium (b), and metal oxides capable of absorbing and desorbing lithium ions (c).

As the carbon material (a), graphite, amorphous carbon, diamond-like carbon, carbon nanotubes, or a composite thereof can be used. Graphite having high crystallinity has high electrical conductivity and has excellent adhesiveness to a negative electrode current collector formed of a metal, such as copper, and excellent voltage flatness. On the other hand, in amorphous carbon having low crystallinity, the volume expansion is relatively small, and therefore, the effect of relieving the volume expansion of the entire negative electrode is large, and deterioration caused by nonuniformity, such as grain boundaries and defects, does not occur easily. The carbon material (a) can be used alone or in combination with other materials.

As the metal (b), a metal mainly composed of Al, Si, Pb, Sn, Zn, Cd, Sb, In, Bi, Ag, Ba, Ca, Hg, Pd, Pt, Te, La, and the like, or alloys of two or more of these, or alloys of these metals or alloys with lithium, or the like can be used. Particularly, the metal (b) preferably comprises silicon (Si). The metal (b) may be used alone or in combination with other materials.

As the metal oxide (c), silicon oxide (for example, SiO and $SiO_2$), aluminum oxide, tin oxide (for example, SnO and $SnO_2$), indium oxide, zinc oxide, lithium oxide, $LiFe_2O_3$, $WO_2$, $MoO_2$, $CuO$, $Nb_3O_5$, $Li_xTi_{2-x}O_4$ ($1 \leq x \leq 4/3$), $PbO_2$, $Pb_2O_5$ or a composite thereof can be used. Particularly, the metal oxide (c) preferably comprises silicon oxide. This is because silicon oxide is relatively stable and does not easily cause reactions with other compounds. In addition, one or two or more elements selected from nitrogen, boron, and sulfur can also be added to the metal oxide (c), for example, in an amount of 0.1 to 5% by weight. By doing this, the electrical conductivity of the metal oxide (c) may be improved. The metal oxide (c) may be used alone or in combination with other materials.

Among these, silicon materials (materials comprising silicon, such as Si, silicon alloys, silicon oxides) having large capacity are particularly preferred as the negative electrode active materials. In one embodiment, the silicon material may be used in combination with a carbon material such as graphite. The silicon materials largely expand and contract at the time of insertion and desorption of Li, and thereby electrical contact between active materials may be broken in some cases. The use of the carbon material together with the silicon material makes it possible to maintain the electrical contact, leading to a battery with excellent cycle characteristics and high energy density. Silicon material particles and carbon material particles may be mixed and used, and surfaces of silicon material particles may be coated with the carbon material and used. The content of the silicon material is preferably 10 weight % or more, more preferably 30 weight % or more, still more preferably 70 weight % or more, and may even be 100 weight %, based on the total amount of the negative electrode active material. The 50% particle size of the silicon material is preferably 0.1 µm or more and 10 µm or less, and more preferably 0.2 µm or more and 8 µm or less. When the particle size is too small, the reactivity with the electrolyte solution may be increased, causing drop in life characteristics. When the particle size is too large, the particles easily crack at the time of insertion and desorption of Li, and the lifespan is decreased. The 50% particle size is the median value of a particle size distribution on a volumetric basis. The particle size distribution on a volumetric basis can be measured by a laser diffraction type particle size distribution measuring apparatus.

The binder is not particularly limited, and polyvinylidene fluoride (PVdF), vinylidene fluoride-hexafluoropropylene copolymer, vinylidene fluoride-tetrafluoroethylene copolymer, polytetrafluoroethylene, polypropylene, polyethylene, polybutadiene, polyacrylic acid, polyacrylic ester, polystyrene, polyacrylonitrile, polyimide, polyamide-imide or the like may be used. Also, the binder may be a mixture, a copolymer or a cross-linked body of a plurality of the above resins, for example, styrene butadiene rubber (SBR). When an aqueous binder such as an SBR emulsion is used, a thickener such as carboxymethyl cellulose (CMC) can also be used. The amount of the binder is preferably 0.5 to 20 parts by weight based on 100 parts by weight of the negative electrode active material from the viewpoint of sufficient binding strength and high energy density that are in a trade-off relation with each other.

In one aspect of the present embodiment, a polyacryric acid comprising a (meth)acrylic acid monomer unit represented by the following formula (10) may be used. Herein, the term "(meth)acrylic acid" means acrylic acid and methacrylic acid.

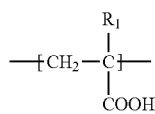
(10)

In formula (10), $R^1$ is a hydrogen atom or a methyl group.

The carboxylic acid in a monomer unit represented by formula (10) may be a carboxylic acid salt, such as a carboxylic acid metal salt. The metal is preferably a monovalent metal. Examples of the monovalent metal include alkali metals (for example, Na, Li, K, Rb, Cs, Fr and the like) and precious metals (for example, Ag, Au, Cu and the like) and the like. When the polyacrylic acid contains the carboxylic acid salt in at least some monomer units, adhesiveness to constituent materials may be further improved in some cases.

The polyacrylic acid may comprise other monomer units. When the polycarylic acid further comprises monomer units other than the (meth)acrylic acid monomer units, the peel strength between the negative electrode active material layer and the current collector may be improved in some cases. Examples of other monomer units include monomer units derived from monomers, such as acids having ethylenically unsaturated group, for example, monocarboxylic acid compounds such as crotonic acid and pentenoic acid, dicarboxylic acid compounds such as itaconic acid and maleic acid, sulfonic acid compounds such as vinylsulfonic acid, and phosphonic acid compounds such as vinylphosphonic acid; aromatic olefins having acidic group such as styrene sulfonic acid and styrene carboxylic acid; (meth)acrylic acid alkyl esters; acrylonitrile; aliphatic olefins such as ethylene, propylene, and butadiene; aromatic olefins such as styrene; and the like. In addition, other monomer units may be monomer units constituting a known polymer that is used as a binder for a secondary battery. If present, acids may be also replaced with their salts in these monomer units.

In addition, in the polyacrylic acid, at least one hydrogen atom in a main chain and a side chain may be substituted by halogen (fluorine, chlorine, bromine, iodine, etc.) or the like.

When the polyacrylic acid is a copolymer containing two or more types of monomer units, the copolymer may be a random copolymer, an alternating copolymer, a block copolymer, a graft copolymer or combinations thereof.

The lower limit of the content of the polyacrylic acid used in the negative electrode is preferably 1 part by weight or more, and more preferably 2 parts by weight or more, and the upper limit is preferably 20 parts by weight or less, and more preferably 10 parts by weight or less based on 100 parts by weight of the negative electrode active material. Another binder may be used in combination with the polyacrylic acid.

For the negative electrode active material layer, a conductive assisting agent may be added for the purpose of lowering the impedance. Examples of the conductive assisting agent include, flake-like, soot, and fibrous carbon fine particles and the like, for example, graphite, carbon black, acetylene black, vapor grown carbon fibers and the like.

As the negative electrode current collector, from the viewpoint of electrochemical stability, aluminum, nickel, stainless steel, chrome, copper, silver, or an alloy thereof may be used. As the shape thereof, foil, flat plate, mesh and the like are exemplified.

The negative electrode according to the present embodiment may be prepared, for example, by preparing a negative electrode slurry comprising the negative electrode active material, the binder and a solvent and applying this to the negative electrode current collector to form the negative electrode active material layer. Examples of a method for forming the negative electrode active material layer include a doctor blade method, a die coater method, a CVD method, a sputtering method, and the like. After forming the negative electrode active material layer in advance, a thin film of aluminum, nickel or an alloy thereof as a negative electrode current collector may be formed thereon by a method such as vapor deposition or sputtering, to prepare a negative electrode.

<Separator>

The separator may be of any type as long as it has durability against the electrolyte solution. Specific examples of a material thereof include polyolefins such as polypropylene and polyethylene, cellulose, polyesters such as polyethylene terephthalate and polybutylene terephthalate, polyimide, polyamide-imide, polyvinylidene fluoride, aromatic polyamides (aramid) such as polymetaphenylene isophthalamide, polyparaphenylene terephthalamide and copolyparaphenylene 3,4'-oxydiphenylene terephthalamide, and the like. These can be used as porous films, woven fabrics, nonwoven fabrics or the like.

<Insulation Layer>

An insulation layer may be formed on a surface of the positive electrode, the negative electrode and the separator.

Examples of a method for forming the insulation layer include a doctor blade method, a die coater method, a CVD method, a sputtering method, and the like. The insulation layer may be formed at the same time as forming the positive electrode active material layer, negative electrode active material layer or separator. Materials constituting the insulation layer include a mixture of an insulating filler such as aluminum oxide or barium titanate and a binder such as styrene butadiene rubber or polyvinylidene fluoride.

<Structure of Secondary Battery>

Figure 2:
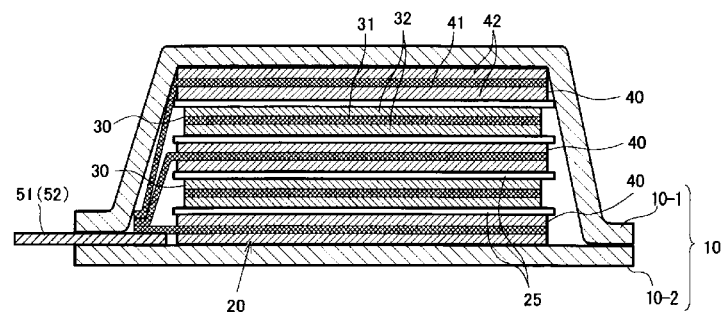
FIG. 2 is a cross-sectional view schematically showing a cross section of the battery of FIG. 1.

The lithium ion secondary battery according to the present embodiment may have, for example, a structure as shown in FIGS. 1 and 2. This secondary battery comprises a battery element 20, a film outer package 10 housing the battery element 20 together with an electrolyte, and a positive electrode tab 51 and a negative electrode tab 52 (hereinafter these are also simply referred to as "electrode tabs").

In the battery element 20, a plurality of positive electrodes 30 and a plurality of negative electrodes 40 are alternately stacked with separators 25 sandwiched therebetween as shown in FIG. 2. In the positive electrode 30, an electrode material 32 is applied to both surfaces of a metal foil 31, and also in the negative electrode 40, an electrode material 42 is applied to both surfaces of a metal foil 41 in the same manner. The present invention is not necessarily limited to stacking type batteries and may also be applied to batteries such as a winding type.

As shown in FIGS. 1 and 2, the lithium ion secondary battery according to the present embodiment may have an arrangement in which the electrode tabs are drawn out to one side of the outer package, but the electrode tab may be drawn out to both sides of the outer package. Although detailed illustration is omitted, the metal foils of the positive electrodes and the negative electrodes each have an extended portion in part of the outer periphery. The extended portions of the negative electrode metal foils are brought together into one and connected to the negative electrode tab 52, and the extended portions of the positive electrode metal foils are brought together into one and connected to the positive electrode tab 51 (see FIG. 2). The portion in which the extended portions are brought together into one in the stacking direction in this manner is also referred to as a "current collecting portion" or the like.

The film outer package 10 is composed of two films 10-1 and 10-2 in this example. The films 10-1 and 10-2 are heat-sealed to each other in the peripheral portion of the battery element 20 and hermetically sealed. In FIG. 1, the positive electrode tab 51 and the negative electrode tab 52 are drawn out in the same direction from one short side of the film outer package 10 hermetically sealed in this manner. Of course, the electrode tabs may be drawn out from different two sides respectively. In addition, regarding the arrangement of the films, in FIG. 1 and FIG. 2, an example in which a cup portion is formed in one film 10-1 and a cup portion is not formed in the other film 10-2 is shown, but other than this, an arrangement in which cup portions are formed in both films (not illustrated), an arrangement in which a cup portion is not formed in either film (not illustrated), and the like may also be adopted.

<Method for Manufacturing Secondary Battery>

The secondary battery according to the present embodiment can be manufactured by a conventional method. An example of a method for manufacturing a secondary battery will be described taking a stacked laminate type secondary battery as an example. First, in the dry air or an inert atmosphere, the positive electrode and the negative electrode are placed to oppose to each other via a separator to form an electrode element. Next, this electrode element is accommodated in an outer package (container), an electrolyte solution is injected, and the electrodes are impregnated with the electrolyte solution. Thereafter, the opening of the outer package is sealed to complete the secondary battery.

<Assembled battery>

A plurality of the secondary batteries according to the present embodiment may be combined to form an assembled battery. The assembled battery may be configured by connecting two or more secondary batteries according to the present embodiment in series or in parallel or in combination of both. The connection in series and/or parallel makes it possible to adjust the capacitance and voltage freely. The number of the secondary batteries included in the assembled battery can be set appropriately according to the battery capacity and output.

<Vehicle>

The secondary battery or the assembled battery according to the present embodiment can be used in vehicles. Vehicles according to the present embodiment include hybrid vehicles, fuel cell vehicles, electric vehicles (besides four-wheel vehicles (cars, commercial vehicles such as trucks and buses, light automobiles, etc.), two-wheeled vehicle (bike) and tricycle), and the like. The vehicles according to the present embodiment are not limited to automobiles, and it may be a variety of power source of other vehicles, such as a moving body like a train, ship, submarine, satellite or the like.

EXAMPLES

Although the present embodiment will be described in detail referring examples below, the present embodiment is not limited thereto.

In examples, capacity retention rate and resistance increase rate were used as evaluation indexes for batteries. The capacity retention rate is a value (unit: %) calculated by (discharge capacity of the last cycle)/(discharge capacity of the first cycle)×100. The resistance increase rate is a value (unit: %) calculated by [(resistance on the last cycle charge)−(resistance on the first cycle charge)]/(resistance on the first cycle charge)×100.

In each example, compounds described in the following table were used in the preparation of the electrolyte solution.

TABLE 1

| | |
|---|---|
| 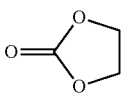 | EC |
| 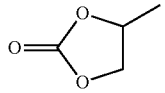 | PC |
| 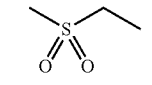 | EMS |
| 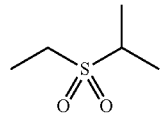 | EiPS |

TABLE 1-continued

| | |
|---|---|
| 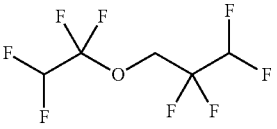 [SMILES: FC(F)C(F)(F)COC(F)(F)C(F)F] | FE |
| 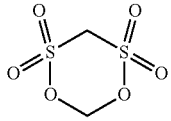 | MMDS |
| 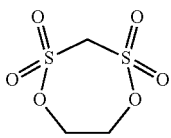 [SMILES: O=S1(=O)CS(=O)(=O)OCCO1] | EMDS |
| 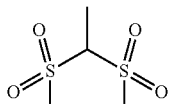 | 3MDT |
| 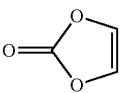 | VC |
| 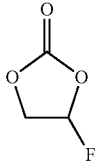 | FEC |
| 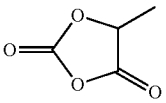 | 5MDD |
| 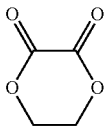 | 14D23D |
| 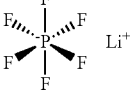 | LiPF$_6$ |
| 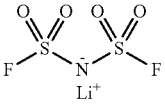 | LiFSI (LiN(FSO$_2$)$_2$) |

Examples 1 to 2 and Comparative Examples 1 to 5

(Positive Electrode)

Li$_{1.15}$Ni$_{0.3}$Mn$_{0.55}$O$_2$, spherical carbon and flaky carbon, and polyvinylidene fluoride (PVdF) were mixed uniformly to prepare a positive electrode mixture. The weight ratio of each component in the positive electrode mixture was set to Li$_{1.15}$Ni$_{0.3}$Mn$_{0.55}$O$_2$:spherical carbon:flaky carbon: PVdF=93:3:1:3. The prepared positive electrode mixture was dispersed into N-methyl-2-pyrrolidone (NMP) to prepare a positive electrode slurry. The positive electrode slurry was uniformly applied to an aluminum foil that was used as a positive electrode current collector, dried at 120° C., and further pressed, and then a positive electrode having a unit weight of 23.8 g/cm$^2$ and a density of 3.0 g/cm$^3$ was provided.

(Negative Electrode)

A carbon-coated silicon oxide (SiOC) having a 50% particle size of 5 μm, in which the weight ratio of the carbon coating to the silicon oxide is 5:95, fibrous carbon, and polyacrylic acid (PAA) were uniformly mixed to prepare a negative electrode mixture. The weight ratio of each component in the negative electrode mixture was set to SiOC: fibrous carbon:PAA=90:2:8. The prepared negative electrode mixture was dispersed into water to prepare a negative electrode slurry. The negative electrode slurry was uniformly applied to a SUS foil that was used as a negative electrode current collector, dried at about 50° C., and further pressed, and then a negative electrode having a unit weight of 3.1 g/cm$^2$ and a density of 1.3 g/cm$^3$ was provided.

(Electrolyte Solution)

First, PC and FE were mixed so as to have a volume ratio described in Table 2, to prepare the electrolyte solvent of each example respectively. Other compounds were dissolved in this electrolyte solvent so as to have concentrations described in Table 2, to prepare the electrolyte solution of each example respectively.

(Assembly of Secondary Battery)

An aluminum tab was ultrasonically welded to the current collector terminal of the positive electrode. A nickel tab was ultrasonically welded to the current collector terminal of the negative electrode. The positive electrode and the negative electrode were stacked via a cellulose separator with a thickness of 20 μm sandwiched therebetween so that the surface coated by the positive electrode mixture and the surface coated by the negative electrode mixture were opposed to each other, to prepare an electrode element. The capacity ratio of the negative electrode and the positive electrode (negative electrode capacity/positive electrode capacity) was set to 1.2. The electrode element was housed in an aluminum laminate exterior film. Three sides of the exterior film except for an injection hole were thermally welded, and this was dried all night and all day. After drying, the produced electrolyte solution was injected so that the amount thereof was 1.4 times the total void volume of the positive electrode, the negative electrode and the separator. The injection hole was thermally welded, and a stacking type lithium ion secondary battery was completed.

(Charge and Discharge Test)

Batteries were subjected to repeating cycles four times under a temperature of 45° C. In each cycle, constant current charging at a current value of 0.1 C to 4.5 V was conducted, and then constant current discharging at a current value of 0.1 C to 1.5 V was conducted. Note that unit C represents a relative current amount, and 0.1 C means a current value at which discharge is completed in just 10 hours when a battery having a capacity of a nominal capacity value is subjected to constant current discharge.

(Degassing)

A side of the thermally welded laminate exterior film was opened, and gas generated at the time of charge and discharge was released under vacuum.

(Evaluation of Battery)

The battery was subjected to constant current charge at a current value of 0.2 C to 4.5 V and subjected to constant current discharge at a current value of 0.3 C to 1.5 V. This operation was repeated 300 times to evaluate cycle characteristics. In each cycle, AC impedance measurement at intervals of 5 mV from 200 kHz to 0.1 Hz was conducted after the constant current charge. The capacity retention rate and the resistance increase rate were calculated from obtained results. Results are shown in Table 2.

3, to prepare the electrolyte solvent of each example respectively. Other compounds were dissolved in this electrolyte solvent so as to have concentrations described in Table 3, to prepare the electrolyte solution of each example respectively.

TABLE 2

|  | $LiPF_6$ [mol/L] | LiFSI [mol/L] | PC [vol %] | FE [vol %] | MMDS [wt %] | VC [wt %] | FEC [wt %] | Resistance increase rate [%] | Capacity retention rate [%] |
|---|---|---|---|---|---|---|---|---|---|
| Example 1 | 0.6 | 0.6 | 70 | 30 | 1 | — | — | 23.0 | 76.5 |
| Example 2 | 0.6 | 0.6 | 70 | 30 | 2 | — | — | 80.5 | 73.5 |
| Comparative example 1 | 0.6 | 0.6 | 70 | 30 | — | — | — | 127.4 | 48.0 |
| Comparative example 2 | 0.6 | 0.6 | 70 | 30 | — | 1 | — | 324.0 | 58.7 |
| Comparative example 3 | 0.6 | 0.6 | 70 | 30 | — | — | 1 | 169.1 | 60.1 |
| Comparative example 4 | 0.6 | 0.6 | 70 | 30 | — | 2 | — | 153.9 | 39.8 |
| Comparative example 5 | 0.6 | 0.6 | 70 | 30 | — | — | 2 | 540.4 | 36.9 |

As shown in Table 2, capacity retention rate was low, and resistance increase rate was high, when vinylene carbonate (VC) or fluoroethylene carbonate (FEC) was used. In particular, when the amount of vinylene carbonate or fluoroethylene carbonate was increased to 2 weight %, capacity retention rate was significantly dropped. Meanwhile, when methylene methanedisulfonic acid ester was used, both the capacity retention rate and the resistance increase rate were significantly improved. These results show the effect of the combination of $LiN(FSO_2)_2$ and the cyclic sulfone acid ester.

Examples 3 to 4 and Comparative Example 6

(Positive Electrode)

$Li_{1.15}Ni_{0.3}Mn_{0.55}O_2$, spherical carbon and flaky carbon, and polyvinylidene fluoride (PVdF) were mixed uniformly to prepare a positive electrode mixture. The weight ratio of each component in the positive electrode mixture was set to $Li_{1.15}Ni_{0.3}Mn_{0.55}O_2$:spherical carbon:flaky carbon: PVdF=93:3:1:3. The prepared positive electrode mixture was dispersed into N-methyl-2-pyrrolidone (NMP) to prepare a positive electrode slurry. The positive electrode slurry was uniformly applied to an aluminum foil that was used as a positive electrode current collector, dried at 120° C., and further pressed, and then a positive electrode having a unit weight of 23.8 g/cm² and a density of 3.0 g/cm³ was obtained.

(Negative Electrode)

A carbon-coated silicon oxide (SiOC) having a 50% particle size of 5 μm, in which the weight ratio of the carbon coating to the silicon oxide is 5:95, spherical carbon, and polyacrylic acid (PAA) were uniformly mixed to prepare a negative electrode mixture. The weight ratio of each component in the negative electrode mixture was set to SiOC: spherical carbon:PAA=87:5:8. The prepared negative electrode mixture was dispersed into water to prepare a negative electrode slurry. The negative electrode slurry was uniformly applied to a SUS foil that is used as a negative electrode current collector, dried at about 50° C., and further pressed, and then a negative electrode having a unit weight of 3.1 g/cm² and a density of 1.3 g/cm³ was obtained.

(Electrolyte solution)

First, solvents selected from EC, PC, EMS, EiPS and FE were mixed so as to have a volume ratio described in Table (Assembly of Secondary Battery)

An aluminum tab was ultrasonically welded to the current collector terminal of the positive electrode. A nickel tab was ultrasonically welded to the current collector terminal of the negative electrode. The positive electrode and the negative electrode were stacked via a cellulose separator with a thickness of 20 μm sandwiched therebetween so that the surface coated by the positive electrode mixture and the surface coated by the negative electrode mixture were opposed to each other, to prepare an electrode element. The capacity ratio of the negative electrode and the positive electrode (negative electrode capacity/positive electrode capacity) was set to 1.2. The electrode element was housed in an aluminum laminate exterior film. Three sides of the exterior film except for an injection hole were thermally welded, and this was dried all night and all day. After drying, the produced electrolyte solution was injected so that the amount thereof was 1.4 times the total void volume of the positive electrode, the negative electrode and the separator. The injection hole was thermally welded, and a stacking type lithium secondary battery was completed.

(Charge and Discharge Test)

Batteries were subjected to repeating cycles four times under a temperature of 45° C. In each cycle, constant current charging at a current value of 0.1 C to 4.5 V was conducted, and then constant current discharging at a current value of 0.1 C to 1.5 V was conducted. Note that unit C represents a relative current amount, and 0.1 C means a current value at which discharge is completed in just 10 hours when a battery having a capacity of a nominal capacity value is subjected to constant current discharge.

(Degassing)

Then a side of the thermally welded laminate exterior film was opened, and gas generated at the time of charge and discharge was released under vacuum.

(Evaluation of Battery)

The battery was subjected to constant current charge at a current value of 0.5 C to 4.5 V and constant voltage charge to a current amount of 0.2 C and subjected to constant current discharge at a current value of 0.5 C to 1.5 V. This operation was repeated 100 times to evaluate cycle characteristics. In each cycle, AC impedance measurement at intervals of 5 mV from 200 kHz to 0.1 Hz was conducted after the constant current charge. The capacity retention rate and the resistance increase rate were calculated from obtained results. Results are shown in Table 3.

Examples 5 to 11 and Comparative Example 7

The production method of an electrolyte solution was the same as in Example 3, and components therein were as shown in Table 3. In the battery evaluation, the current value in the constant current charge was set to 0.3 C, the constant voltage charge was not conducted, the current value in the constant current discharge was set to 0.3 C, and the number of cycles was set to 150. Except for these, batteries were produced and evaluated in the same manner as in Example 3. The capacity retention rate and the resistance increase rate were calculated from obtained results. Results are shown in Table 3.

Examples 12 to 14 and Comparative Example 8

The production method of an electrolyte solution was the same as in Example 3, and components therein were as shown in Table 3. In the battery evaluation, the current value in the constant current charge was set to 0.3 C, the constant voltage charge was not conducted, the current value in the constant current discharge was set to 0.3 C, and the number of cycles was set to 100. Except for these, batteries were produced and evaluated in the same manner as in Example 3. The capacity retention rate and the resistance increase rate were calculated from obtained results. Results are shown in Table 3.

Example 15 and Comparative Example 9

The production method of an electrolyte solution was the same as in Example 3, and components therein were as shown in Table 3. In the battery evaluation, the current value in the constant current charge was set to 0.3 C, the constant voltage charge was not conducted, the current value in the constant current discharge was set to 0.3 C, and the number of cycles was set to 100. Except for these, batteries were produced and evaluated in the same manner as in Example 3. The capacity retention rate and the resistance increase rate were calculated from obtained results. Results are shown in Table 3.

Examples 16 to 21 and Comparative Example 10

The production method of an electrolyte solution was the same as in Example 3, and components therein were as shown in Table 3. In the battery evaluation, the current value in the constant current charge was set to 0.3 C, the constant voltage charge was not conducted, the current value in the constant current discharge was set to 0.3 C, and the number of cycles was set to 50. Except for these, batteries were produced in the same manner as in Example 3. The capacity retention rate and the resistance increase rate were calculated from obtained results. Results are shown in Table 3.

Comparative Examples 11 to 16

The production method of an electrolyte solution was the same as in Example 3, and components therein were as shown in Table 3. In the battery evaluation, the current value in the constant current charge was set to 0.3 C, the constant voltage charge was not conducted, the current value in the constant current discharge was set to 0.3 C, and the number of cycles was set to 50. Except for these, batteries were produced and evaluated in the same manner as in Example 3. The capacity retention rate and the resistance increase rate were calculated from obtained results. Results are shown in Table 3.

TABLE 3

| | $LiPF_6$ [mol/L] | LiFSI [mol/L] | EC [vol %] | PC [vol %] | EMS [vol %] | EiPS [vol %] | FE [vol %] |
|---|---|---|---|---|---|---|---|
| Comparative example 6 | 1.2 | — | — | 70 | — | — | 30 |
| Example 3 | 1.16 | 0.04 | — | 70 | — | — | 30 |
| Example 4 | 0.6 | 0.6 | — | 70 | — | — | 30 |
| Comparative example 7 | 0.6 | 0.6 | — | 70 | — | — | 30 |
| Example 5 | 0.6 | 0.6 | — | 70 | — | — | 30 |
| Example 6 | 0.6 | 0.6 | — | 70 | 10 | — | 20 |
| Example 7 | 0.6 | 0.6 | — | 70 | — | 10 | 20 |
| Example 8 | 0.6 | 0.6 | — | 60 | 10 | — | 30 |
| Example 9 | 0.6 | 0.6 | — | 60 | — | 10 | 30 |
| Example 10 | 0.6 | 0.6 | — | 70 | — | — | 30 |
| Example 11 | 0.6 | 0.6 | — | 70 | — | — | 30 |
| Comparative example 8 | 0.6 | 0.6 | — | 70 | — | — | 30 |
| Example 12 | 0.6 | 0.6 | — | 70 | — | — | 30 |
| Example 13 | 0.6 | 0.6 | — | 70 | — | — | 30 |
| Example 14 | 0.6 | 0.6 | — | 70 | — | — | 30 |
| Comparative example 9 | 0.5 | 0.5 | 5 | — | — | 50 | 45 |
| Example 15 | 0.5 | 0.5 | 5 | — | — | 50 | 45 |
| Comparative example 10 | 0.6 | 0.6 | — | 70 | — | — | 30 |
| Example 16 | 0.6 | 0.6 | — | 70 | — | — | 30 |
| Example 17 | 0.6 | 0.6 | — | 70 | — | — | 30 |
| Example 18 | 0.6 | 0.6 | — | 70 | — | — | 30 |
| Example 19 | 0.6 | 0.6 | — | 70 | — | — | 30 |
| Example 20 | 0.6 | 0.6 | — | 70 | — | — | 30 |
| Example 21 | 0.6 | 0.6 | — | 70 | — | — | 30 |
| Comparative example 11 | 1.2 | — | — | 70 | — | — | 30 |

TABLE 3-continued

| | | | | | | | |
|---|---|---|---|---|---|---|---|
| Comparative example 12 | 1.0 | 0.2 | — | 70 | — | — | 30 |
| Comparative example 13 | 0.8 | 0.4 | — | 70 | — | — | 30 |
| Comparative example 14 | 0.4 | 0.8 | — | 70 | — | — | 30 |
| Comparative example 15 | 0.2 | 1.0 | — | 70 | — | — | 30 |
| Comparative example 16 | — | 1.2 | — | 70 | — | — | 30 |

| | MMDS [vol %] | EMDS [wt %] | 3MDT [wt %] | 5MDD [wt %] | 14D23D [wt %] | Resistance increase rate [%] | Capacity retention rate [%] |
|---|---|---|---|---|---|---|---|
| Comparative example 6 | — | — | — | — | — | 5.6 | 87.7 |
| Example 3 | 0.5 | — | — | — | — | −1.4 | 87.5 |
| Example 4 | 1.0 | — | — | — | — | −7.8 | 88.6 |
| Comparative example 7 | — | — | — | — | — | 11.8 | 85.4 |
| Example 5 | 1.0 | — | — | — | — | 5.0 | 89.4 |
| Example 6 | 1.0 | — | — | — | — | 5.2 | 89.1 |
| Example 7 | 1.0 | — | — | — | — | 6.9 | 87.6 |
| Example 8 | 1.0 | — | — | — | — | 6.5 | 88.8 |
| Example 9 | 1.0 | — | — | — | — | 3.6 | 89.8 |
| Example 10 | 1.0 | — | — | 0.5 | — | 4.1 | 89.7 |
| Example 11 | 1.0 | — | — | — | 0.5 | 3.9 | 89.8 |
| Comparative example 8 | — | — | — | — | — | 8.3 | 90.1 |
| Example 12 | 1.0 | — | — | — | — | 6.7 | 91.7 |
| Example 13 | — | 1.0 | — | — | — | 14.0 | 91.7 |
| Example 14 | — | — | 1.0 | — | — | 1.2 | 91.2 |
| Comparative example 9 | — | — | — | — | — | −1.9 | 94.0 |
| Example 15 | 1.0 | — | — | — | — | −3.7 | 94.0 |
| Comparative example 10 | — | — | — | — | — | — | 95.7 |
| Example 16 | 0.1 | — | — | — | — | — | 95.6 |
| Example 17 | 0.2 | — | — | — | — | — | 95.6 |
| Example 18 | 0.4 | — | — | — | — | — | 97.1 |
| Example 19 | 0.6 | — | — | — | — | — | 97.3 |
| Example 20 | 0.8 | — | — | — | — | — | 96.6 |
| Example 21 | 1.0 | — | — | — | — | — | 96.6 |
| Comparative example 11 | — | — | — | — | — | — | 95.7 |
| Comparative example 12 | — | — | — | — | — | — | 96.0 |
| Comparative example 13 | — | — | — | — | — | — | 96.2 |
| Comparative example 14 | — | — | — | — | — | — | 96.8 |
| Comparative example 15 | — | — | — | — | — | — | 95.2 |
| Comparative example 16 | — | — | — | — | — | — | 88.8 |

This application claims priority right based on Japanese patent application No. 2017-175586, filed on Sep. 13, 2017, and the entire disclosure of which is hereby incorporated by reference.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

INDUSTRIAL APPLICABILITY

The lithium ion secondary battery according to the present embodiment can be utilized in, for example, all the industrial fields requiring a power supply and the industrial fields pertaining to the transportation, storage and supply of electric energy. Specifically, it can be used in, for example, power supplies for mobile equipment such as cellular phones and notebook personal computers; power supplies for electrically driven vehicles including an electric vehicle, a hybrid vehicle, an electric motorbike and an electric-assisted bike, and moving/transporting media such as trains, satellites and submarines; backup power supplies for UPSs; and electricity storage facilities for storing electric power generated by photovoltaic power generation, wind power generation and the like.

EXPLANATION OF SYMBOLS

10 film outer package
20 battery element
25 separator
30 positive electrode
40 negative electrode

The invention claimed is:

1. A lithium ion secondary battery comprising
a positive electrode comprising a positive electrode active material that operates at 4.5 V or more with respect to lithium, and
an electrolyte solution comprising an electrolyte solvent comprising propylene carbonate in an amount of 60 volume % or more and a fluorinated ether represented by formula (1), a cyclic sulfonic acid ester represented by formula (2) and LiN(FSO$_2$)$_2$,

$$C_nH_{2n+1-l}F_l\text{—O—}C_mH_{2m+1-k}F_k \quad (1)$$

wherein n is 1, 2, 3, 4, 5 or 6, m is 1, 2, 3 or 4, l is an integer of 0 to 2n+1, k is an integer of 0 to 2m+1, and at least one of l and k is 1 or more,

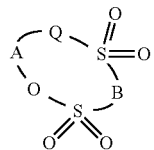

(2)

wherein Q represents an oxygen atom, a methylene group or a single bond, A represents a substituted or unsubstituted alkylene group having 1 to 6 carbon atoms; a carbonyl group, a sulfinyl group, a substituted or unsubstituted fluoroalkylene group having 1 to 6 carbon atoms or a group having 2 to 6 carbon atoms in which alkylene units or fluoroalkylene units are bonded through an ether bond, and B represents a substituted or unsubstituted alkylene group having 1 to 6 carbon atoms, a substituted or unsubstituted fluoroalkylene group having 1 to 6 carbon atoms or an oxygen atom,
wherein a concentration of LiN(FSO$_2$)$_2$ in the electrolyte solution is 0.4 mol/L or more, and
the positive electrode active material is represented by the following formula (G):

$$\text{Li}(\text{Li}_x\text{M}_y\text{Mn}_z)\text{O}_2 \quad (G)$$

wherein in formula (G), x, y, and z satisfy 0.1≤x<0.3, 0.1≤y≤0.4, 0.33≤z≤0.7 and x+y+z=1, and M is at least one selected from the group consisting of Li, Co and Ni.

2. The lithium ion secondary battery according to claim 1, wherein the concentration of LiN(FSO$_2$)$_2$ in the electrolyte solution is 0.5 mol/L or more.

3. The lithium ion secondary battery according to claim 1, wherein the electrolyte solution comprises LiPF$_6$.

4. The lithium ion secondary battery according to claim 1, wherein a content of the fluorinated ether represented by formula (1) in the electrolyte solvent is 1 volume % or more and 30 volume % or less.

5. The lithium ion secondary battery according to claim 1, wherein a content of the cyclic sulfonic acid ester represented by formula (2) in the electrolyte solution is 0.1 weight % or more and 10 weight % or less.

6. The lithium ion secondary battery according to claim 1, wherein the lithium ion secondary battery comprises a negative electrode comprising a silicon material.

7. A vehicle equipped with the lithium ion secondary battery according to claim 1.

8. A method for manufacturing a lithium ion secondary battery, comprising the steps of:
fabricating an electrode element by stacking a positive electrode and a negative electrode via a separator, and
enclosing the electrode element and an electrolyte solution into an outer package,
wherein the positive electrode comprises a positive electrode active material that operates at 4.5 V or more with respect to lithium, and
the electrolyte solution comprises an electrolyte solvent comprising propylene carbonate in an amount of 60 volume % or more and a fluorinated ether represented by formula (1), a cyclic sulfonic acid ester represented by formula (2) and LiN(FSO$_2$)$_2$,

$$C_nH_{2n+1-l}F_l\text{—O—}C_mH_{2m+1-k}F_k \quad (1)$$

wherein n is 1, 2, 3, 4, 5 or 6, m is 1, 2, 3 or 4, l is an integer of 0 to 2n+1, k is an integer of 0 to 2m+1, and at least one of l and k is 1 or more,

(2)

wherein Q represents an oxygen atom, a methylene group or a single bond, A represents a substituted or unsubstituted alkylene group having 1 to 6 carbon atoms; a carbonyl group, a sulfinyl group, a substituted or unsubstituted fluoroalkylene group having 1 to 6 carbon atoms or a group having 2 to 6 carbon atoms in which alkylene units or fluoroalkylene units are bonded through an ether bond, and B represents a substituted or unsubstituted alkylene group having 1 to 6 carbon atoms, a substituted or unsubstituted fluoroalkylene group having 1 to 6 carbon atoms or an oxygen atom,
wherein a concentration of LiN(FSO$_2$)$_2$ in the electrolyte solution is 0.4 mol/L or more, and
the positive electrode active material is represented by the following formula (G):

$$\text{Li}(\text{Li}_x\text{M}_y\text{Mn}_z)\text{O}_2 \quad (G)$$

wherein in formula (G), x, y, and z satisfy 0.1≤x<0.3, 0.1≤y≤0.4, 0.33≤z≤0.7 and x+y+z=1, and M is at least one selected from the group consisting of Li, Co and Ni.

9. The lithium ion secondary battery according to claim 1, wherein the concentration of LiN(FSO$_2$)$_2$ in the electrolyte solution is 0.4 mol/L or more and 3 mol/L or less.

10. The lithium ion secondary battery according to claim 1, wherein a content of the cyclic sulfonic acid ester represented by formula (2) in the electrolyte solution is 0.3 weight % or more.

* * * * *